United States Patent [19]

Threlkel

[11] Patent Number: 4,757,042
[45] Date of Patent: Jul. 12, 1988

[54] OLEFIN OLIGOMERIZATION CATALYST

[75] Inventor: Richard S. Threlkel, El Cerrito, Calif.

[73] Assignee: Chevron Research Company, San Francisco, Calif.

[21] Appl. No.: 45,027

[22] Filed: May 1, 1987

Related U.S. Application Data

[62] Division of Ser. No. 896,897, Aug. 15, 1986, Pat. No. 4,677,241.

[51] Int. Cl.$^4$ ............................ C08F 4/60; B01J 31/14
[52] U.S. Cl. ...................................... 502/112; 502/117
[58] Field of Search ................ 502/117, 112; 585/512, 585/513, 515, 526

[56] References Cited

U.S. PATENT DOCUMENTS

| | | | |
|---|---|---|---|
| 3,354,236 | 11/1967 | Klein | 585/515 |
| 3,424,815 | 2/1969 | Cannell et al. | 502/117 X |
| 3,577,395 | 5/1971 | Lal et al. | 260/82.1 |
| 3,592,870 | 7/1971 | Dunn | 502/117 X |
| 3,790,551 | 2/1974 | Yagi et al. | 260/94.3 |
| 3,910,869 | 10/1975 | Throckmorton | 260/94.3 |
| 4,065,512 | 12/1977 | Cares | 585/515 |
| 4,069,273 | 1/1978 | Komoto | 585/512 |
| 4,102,817 | 7/1978 | Throckmorton et al. | 252/429 B |
| 4,124,627 | 11/1978 | Fahey | 585/514 |
| 4,187,197 | 2/1980 | Kabanov et al. | 252/431 P |
| 4,366,087 | 12/1982 | Le Pennec et al. | 585/502 |
| 4,677,241 | 6/1987 | Threlkel | 585/526 |

OTHER PUBLICATIONS

Callahan et al., J. Chem. Soc., Chem. Communication, 1969, pp. 399-400.
Cooke et al., J. Chem. Soc., Section A, 1968, pp. 170-173.
Nyholm et al., J. Chem. Soc., Section A, 1968, pp. 38-40.
Pillai et al., "Dimerization of Ethylene and Propylene Catalyzed by Transition Metal Complexes," Chev. Rev., 1986, pp. 353-399.

*Primary Examiner*—Patrick P. Garvin
*Attorney, Agent, or Firm*—S. R. La Paglia; R. C. Gaffney; L. S. Squires

[57] ABSTRACT

A polymerization catalyst comprising a complex of nickel or palladium and certain fluoro-organo sulfur ligands and an organometal reducing agent. The catalyst is especially useful for the oligomerization of olefins to higher molecular weight olefins having a high degree of linearity.

10 Claims, No Drawings

OLEFIN OLIGOMERIZATION CATALYST

CROSS-REFERENCE TO RELATED APPLICATION

This is a division of application Ser. No. 896,897, filed Aug. 15, 1986 and now U.S. Pat. No. 4,677,241.

BACKGROUND OF THE INVENTION

This invention relates to an improved olefin oligomerization process and catalyst for preparing $C_6$-$C_{30}$ olefin products. In another aspect, the invention relates to a method for preparing said catalyst.

Olefin oligomers are used for a variety of industrial products and have been produced by a variety of catalytic processes. For example, U.S. Pat. No. 3,424,815 describes the preparation of alpha-olefin oligomers using a catalyst comprising the product of certain nickel chelates with a halide-free organoaluminum compound such as alkyl aluminum alkoxides. Patentee teaches that the nickel chelating ligand-anion is substituted with electron withdrawing groups, i.e., nitro, halo, cyano or carboalkoxy and that superior results are obtained when the chelating ligands are halogenated organic ligands.

U.S. Pat. No. 3,592,870 discloses olefin dimerization catalysts formed from an organoaluminum compound and one of the following nickel complexes: (a) bis(beta-mercaptoethylamine)nickel (II) complex; (b) alpha-diketobis(beta-mercaptoethylimine)nickel (II) complex; (c) S,S-disubstituted bis(beta-mercaptoethylamine) nickel (II) complex; or (d) S,S-disubstituted-alpha-diketone bis(beta-mercaptoethylimine)nickel (II) complex. Under (c) and (d) are included complexes of the formulas:

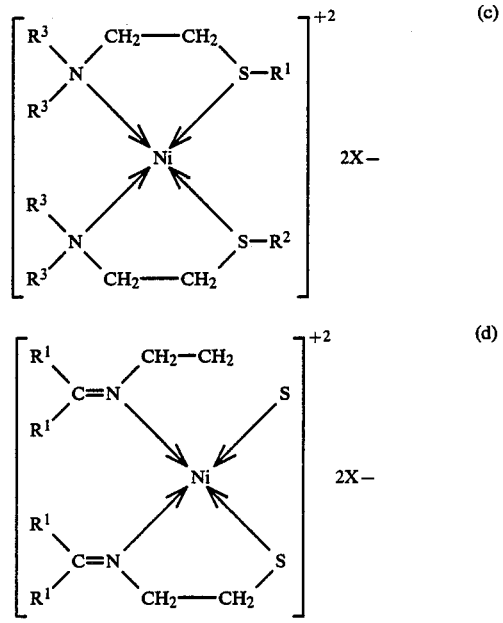

wherein X is halide and $R_1$ and $R_2$ are certain enumerated organic radicals and $R_3$ is as defined for $R_2$ or hydrogen.

U.S. Pat. No. 4,069,273 describes a process for dimerizing low molecular weight linear alpha-olefins using a complex of bis(1,5-cyclooctadiene)nickel and hexafluoro-2,4-pentanedione as the catalyst. Patentee describes his process as producing a highly linear olefin product. U.S. Pat. No. 4,366,087 describes a process for oligomerizing olefins using a catalyst containing a nickel compound having the formula $(R_1COO)(R_2COO)Ni$, wherein $R_1$ is a hydrocarbyl radical having at least 5 carbon atoms and $R_2$ is a haloalkyl radical and an organic aluminum halide. As can be seen from the examples in this patent, patentee's process afforded a product containing a large amount of branched olefins. A number of catalyst systems used for the polymerization of olefins are described in Chemical Review 86 (1986) pp. 353–399.

One of the principal uses of $C_6$-$C_{30}$ olefins is as intermediates for detergents, e.g., sulfonated alkyl benzenes. When used for this purpose, the $C_6$-$C_{30}$ olefin product should have a high proportion of linear olefins because detergents produced from linear olefins are generally more readily biodegraded than those produced with branched olefins. Similarly, mono-branched olefins are generally more readily biodegraded than multibranched olefins and accordingly, more desirable for detergents.

SUMMARY OF THE INVENTION

The present invention provides an oligomerization process and catalyst which produces excellent yields of olefin oligomers having a high proportion of linear olefins, typically on the order of 80% by weight or more and a combination of linear olefins plus mono-branched olefins content on the order of 90% by weight or more. Thus, the present process is especially applicable for the production of olefins for detergents or other surfactants, where biodegradability is important.

The catalyst system of the present invention comprises (1) nickel or palladium complexed with certain fluoro-organothiol or sulfide ligands and a reducing agent selected from the group of organic aluminum halides- or alkoxides- and borohydrides.

The present process for preparing the catalyst of the invention, comprises contacting nickel or palladium or a salt thereof with a fluoro-organothiol or sulfide followed by the addition of said organic aluminum halide or alkoxide or borohydride.

Broadly, the oligomerization process of the present invention comprises contacting a $C_2$-$C_8$ olefin (e.g., propylene, 2-hexene, 4-octene, etc.) with the present catalyst under reactive (oligomerization) conditions.

The invention will be further described herein below.

FURTHER DESCRIPTION OF THE INVENTION AND PREFERRED EMBODIMENTS

The nickel or palladium complex portion of the present catalyst can be described as a complex formed by a salt of nickel or palladium with an organic ligand having at least one fluoro substituent and one —SR substituent wherein R is hydrogen or an optionally substituted hydrocarbyl, for example, alkyl, alkenyl, alkynyl, aryl, alkylaryl, arylalkyl all of which can be optionally substituted with one or more substituents, such as, for example, independently selected from the group of halogen, oxygen, and hydrogen. Typically the fluoro-organothiol or sulfide is polysubstituted with respect to the fluoro substituents. As will be explained hereinbelow, the fluoro-organothiol or sulfide is typically monosubstituted with respect to the —SR substituent. The ligand should not contain any other ligating atom in a ligation position which will displace fluorine as the ligand including a second sulfur substituent. Such atoms or substituents are phosphorous, arsenic, selenium, tellurium or the coordinating forms of nitrogen (e.g., amines, cyclic amines, pyridines, heterocyclic amines) or as noted above, a second sulfur atom. Preferably, the ligand should also not contain chloro or bromo substituents in ligating positions though said substituents are not as deleterious as the aforementioned atoms or substituents. The fluoro-organothiol or sulfide can contain such atoms or substituents provided they are positioned on the molecular such that they do ligate with the nickel or palladium moiety of the complex.

It is conjectured that in the present catalyst the fluoro substituent as well as the sulfur substituent or moiety ligates with the nickel or palladium atom, although technically, it may be more accurate to say that a complex is formed because fluoro is such a weak ligand that it may not be performing as a traditional chelating ligand in the complex. It is further conjectured that the fluoro moiety provides the linear selectivity in the present catalyst and that the stronger ligating groups reduce or destroy the linear selectivity by displacing the fluoro substituent in the complex.

It has further been discovered that greatly superior results (e.g., enhanced activity and selectivity) are obtained by using a fluoro-organic sulfur compound wherein at least one of the fluoro substituents is on a carbon atom adjacent the carbon atom containing the sulfur substituent. Examples of this structural part of the fluoro-organo sulfur compound can be represented by the following partial formulas:

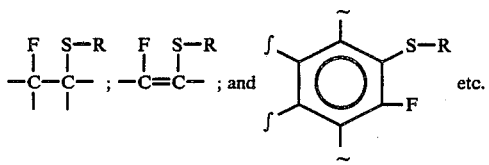

Suitable fluoro-organic thiols which can be used include, for example, those having the formula $(F)_m Z(SR)$ wherein Z is $C_2$–$C_8$ alkyl; $C_2$–$C_8$ alkenyl; aryl having 6 to 10 carbon atoms; arylalkyl, having 6 to 10 carbon atoms in the aryl substituent and 1 to 4 carbon atoms in the alkyl moiety; alkanoyl having 2 to 8 carbon atoms, alkanoylalkylene having 2 to 8 carbon atoms in the alkanoyl moiety and 1 to 6 carbon atoms in the alkylene moiety, or benzoyl; all of which can be optionally substituted with lower alkyl, lower haloalkyl, lower alkenyl, lower haloalkenyl, halo, $C_1$–$C_8$ alkoxy nitro, or cyano. R is hydrogen or independently selected from the same groups as set forth hereinabove with respect to $R^1$; and m is an integer from 1 to 15, dependent upon the size of the organic moiety Z and typically is 1–6.

Examples of ligands encompassed within the above formula include, for example, pentafluorophenylthiol; 2-fluorothiophenol; 2-fluoroethylthiol; 2-fluorothioacetaldehyde; 2-ethylthio-1-fluoroethylene; 3-(4-fluorobutylthio)-4-fluoropent-1-ene; 2,3-difluorophenylthiol; 2-fluoro-4-chlorobenzylthiol; 1-mercapto-2,3,4-trifluorobenzene; trifluorthioacetic-S-acid; pentafluorphenylmethyl mercaptan, and the like.

Preferred fluoro-organic thiols and sulfides are those having the formula $R_1SR$ wherein $R_1$ is fluoroalkyl having 1 to 20 fluoro atoms and 2 to 8 carbon atoms; fluoroaryl having 1 to 7 fluoro atoms and 6 to 10 carbon atoms; fluoroarylalkyl having 1 to 5 fluoro-ring substituents and 1 to 4 carbon atoms in the alkyl moiety; fluoroalkanoyl having 1 through 13 fluoro substituents and 2 to 6 carbon atoms; fluoroalkanoylalkylene having 1 through 13 fluoro substituents and 2 to 6 carbon atoms in the alkanoyl moiety and 1 to 4 carbon atoms in the alkylene moiety and wherein said fluoro substituents can be on either the alkanoyl or alkylene moiety or both; aryl having 6 to 10 carbon atoms or arylalkyl having 6 to 10 carbon atoms in the aryl moiety and 1 to 4 carbon atoms in the alkyl moiety optionally substituted with 1 to 4 fluoro groups and with the proviso that a carbon atom adjacent the carbon atom containing the sulfur substituent is substituted with at least one fluoro group and R is hydrogen, $C_1$–$C_8$ alkyl; $C_2$–$C_8$ alkenyl, aryl having 6 to 10 carbon atoms or arylalkyl, having 6 to 10 carbon atoms in aryl moiety and 1 to 4 carbon atoms in the alkyl moiety; alkanoyl having 2 to 8 carbon atoms; alkanoylalkylene having 2 to 8 carbon atoms in the alkanoyl moiety and 1 to 4 carbon atoms in the alkylene moiety; substituted groups selected from the same groups as set forth hereinabove with respect to R substituted with from 1 to 6 substituents indpendently selected from the group of lower alkyl, lower haloalkyl having 1 to 4 halo substituents, halo, lower haloalkenyl, or lower alkoxy.

Typically, best results have been obtained using pentafluorophenylthiol; methyl pentafluorophenyl mercaptan and ortho-fluorobenzenethiol. It is also noted that unlike the catalyst complexes described in U.S. Pat. No. 3,592,870 in which complexing likes place with respect to the ammonia or amine moiety and sulfur moiety, in the present case the complex is formed with respect to the sulfur moiety and probably the fluoride moiety. Hence, the ligands used in the present catalyst do not require an ammonium or amine substituent or component and as already discussed above, such substituents or other substituents chelating with nickel or palladium in preference to fluorine would be deleterious to the present catalyst.

The nickel and palladium complexes can be prepared by contacting the appropriate fluoro-organic thiol or sulfide complexing agent with nickel or palladium or a suitable salt thereof. Because of solubility considerations, it is preferred to use a nickel salt or palladium salt rather than the elemental metal. This treatment is typically conducted at temperatures in the range of about from $-10°$ to $180°$ C., preferably $25°$ to $60°$ C. for about from 0 to 2 hours, preferably from 0 to ½ hour using about from 1 to 5 moles, preferably 1 to 2 moles of complexing agent per mole of nickel or palladium. The treatment is typically conducted in an organic medium, such as, for example, chlorobenzene, methylene chloride, olefin and the like, and optionally in the presence of a solubilizing agent which converts nickel or palladium in situ into a soluble salt. Suitable salts which can be used include, for example, chlorides, bromides, iodides, sulfates, nitrates and carboxylates of nickel or palladium, and the like. The carboxylate salts described in U.S. Pat. No. 4,366,087 can also be used.

The organoaluminum halide or organoaluminum alkoxide or borohydride reducing agent can then be admixed with the fluorothionickel or fluorothiopalladium complex. The organoaluminum halides and alkoxides include, for example, those represented by the formula $R^*_m AlX_n$ wherein $R^*$ is $C_1$–$C_8$ alkyl, aryl having 6 to 10 carbon atoms or arylalkyl having 6 to 10 carbon atoms in the aryl moiety and 1 to 4 carbon atoms in the alkyl moiety; X is fluoride, chloride, bromide iodide or $C_1$–$C_8$ alkoxide and m is 1 or 2 and n is $3-m$.

Suitable, organic aluminum halides and alkoxides which can be used include, for example, alkyl aluminum halide (e.g., dimethyl aluminum chloride, ethyl aluminum sesquichloride; dipropyl aluminum bromide; dibutyl aluminum iodide; methyl aluminum sesqui fluoride; aryl and arylalkyl aluminum halides (e.g., phenyl; aluminum sesquiiodide; dibenzyl aluminum chloride; alkyl aluminum alkoxides (e.g., diethyl aluminum ethoxide); ethyl aluminum diethoxide; aryl and arylalkyl aluminum alkoxides (e.g., phenyl aluminum diethoxide; dibenzyl aluminum t-butoxide); and the like.

Typically, the organoaluminum halide or alkoxide or borohydride is added to fluorothionickel or fluorothiopalladium complex at temperatures in the range of about from 0° to 150° C. preferably, 20° to 90° C. using about from 1 to 7 moles of organic aluminum halide or alkoxide.

Where the oligomerization is conducted as a batch process, the catalyst can be conveniently prepared in situ in the reactor followed by the addition of the olefin feed stock. The oligomerization can also be conducted as a continuous, semi-batch or multi-step process. The oligomerization can be conducted using suitable equipment and process detail such as are, for example, conventionally employed in this art. Typically, the oligomerization is conducted as a liquid phase reaction by contacting the olefin feedstock, which can be a single olefin or, as is frequently the case, a mixture of olefins, with the present catalyst at temperatures in the range of about from 0° to 120° C., preferably 50° to 90° C. using a feedstock to catalyst ratio of about from 0.00001 to 0.01, of catalyst per mole of olefin feed. The polymerization is generally conducted at pressures in the range of about from 1 to 45 atmospheres, and preferably at least sufficient to maintain a liquid phase system.

The present process and catalyst is especially useful for the oligomerization of propylene feedstocks to produce high yield of $C_6$-$C_{30}$ olefin oligomers having a high proportion of linear oligomers. The product oligomers can be isolated from the reaction product mixture by any suitable procedures, for example, distilltion, extraction, and the like. If higher molecular weight polymers are desired, the linear olefins can be separated and the oligomerization repeated. Unreacted feedstock and lower molecular weight olefins can be recycled back to the initial feedstock. Where linear products are desired, substantially linear olefins (i.e., having a linearity of at least about 80% by weight, should also be used as the feedstock.

It should also be appreciated that where typical or preferred process conditions (e.g., reaction temperatures, times, mole ratios of reactants, catalyst ratio, type of solvents, etc.) have been given, that other process conditions could also be used. Optimum reaction conditions (e.g., temperature, reaction time, reactant ratios, catalyst ratios, solvents, etc.) may vary with the particular reagents or organic solvents used but can be determined by routine optimization procedures.

Definitions

As used herein, the following terms have the following meanings unless expressly stated to the contrary:

The term "lower alkyl" refers to both straight- and branched-chain alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkene" or "lower olefin" refers to both straight-chained and branched-chained olefins groups having 2 through 8 carbon atoms, preferably 2 through 4 carbon atoms. In the present process the olefin feedstocks are preferably highly linear (i.e., straight-chained).

The term "lower alkoxy" refers to the group —OR' wherein R' is lower alkyl.

The term "alkanoyl" refers to the group having the formula:

wherein R' is alkyl having 1 to 7 carbon atoms, preferably 1 to 5 carbon atoms. Typical alkanoyl groups include, for example, acetyl, propionyl, $CH_3CH(CH_3)C(O)$—; $CH_3(CH_2)_6C(O)$—and the like.

The terms "alkanoylalkyl"; alkanoylalkylene" and alkanoylalkylidene" refer to the group

wherein R' is as defined with respect alkanoyl and R" is alkylene having 1 to 6 carbon atoms, preferably 1 to 4 carbon atoms, and can be straight- or branched-chained. Typical "alkanoylalkyl" groups include, for example, —$CH_2C(O)CH_3$; —$CH(CH_3)C(O)C_2H_5$, —$CH_2CH_2C(O)CH_2CH(CH_3)_2$ and the like.

The term "halo" refers to the group of fluoro, chloro, bromo and iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "arylalkylene" or "arylalkyl" refers to the group $ArR^3$—wherein Ar is aryl and $R^3$ is alkylene having 1 through 3 carbon atoms and includes both straight-chained and branched-chained alkylenes, for example, methylene, ethyl, 1-methylethyl, and propyl.

The term "(substituted aryl)alkylene" or "substituted arylalkyl" refers to the group $Ar'R^3$—wherein Ar' is substituted aryl and $R^3$ is alkylene as defined with respect to arylalkylene.

The term "$l_3$ to $l_3$" is intended to include both the lower and upper variable.

A further understanding of the invention can be had from the following non-limiting examples.

EXAMPLES

EXAMPLE 1

Preparation of Nickel Bis(Fluorothiolate)

3.4 Grams of pentafluorothiophenol dissolved in 15 ml of acetone were added dropwise to a filtered solution of 1.83 gr of nickel acetate $4H_2O$ in 50 mls of 1:1 acetone/water. The slow addition of 150 mls of water caused the precipitation of brown nickel bis(pentafluorophenylthiolate). Filtration and drying in a vacuum oven gave 2.9 gr of bis-thiolate.

Palladium bis(pentafluorophenylthiolate) can be prepared by applying the above procedure using palladium acetate in place of nickel acetate.

EXAMPLE 2 marized in Table 1 hereinbelow wherein percentages refer to weight percents.

TABLE 1

| Olefins | Example 2 | | Example 3 | | Example 4 | | Example 5 | |
|---|---|---|---|---|---|---|---|---|
| | Weight % | L* % | Weight % | L* % | Weight % | L* % | Weight % | L* % |
| $C_6=$ | 42.2% | 80% | 46.2% | 74% | 48% | 79% | 85% | 23% |
| $C_9=$ | 30.2% | 69% | 33.5% | 57% | 30% | 56% | 14% | 5% |
| $C_{12}=$ | 11.5% | 49% | 13.3% | 28% | 12% | 47% | 1% | — |
| $C_{15}=$ | 4.5% | 37% | 4.8% | 19% | 4% | — | — | — |
| $C_{18}=$ | 2% | 35% | 1.4% | 19% | 2% | — | — | — |
| $C_{21}=+$ | 9% | — | 1% | — | 4% | — | — | — |

*L = Linearity

Oligomerization of Propylene-Nickel Catalyst Complex

229 Mgs of nickel bis(pentafluorophenylthiolate) was slurried in 5 gr of chlorobenzene and was transferred to a stirrer bomb and sealed. 480 Mgs of 25 wt. % solution of diethyl aluminum chloride in heptane was added to 5 gr of chlorobenzene and transferred to a hoke bomb. The hoke bomb was pressured with 110 psi of propylene and attached to the stirrer bomb. After flushing the stirrer bomb two times with propylene, the diethyl aluminum chloride solution was blown into the reactor at 60° C. and the propylene pressure in the reactor adjusted to 130 psi. After 20 hours, 6.23 gr of products were obtained with the distribution shown in Table 1 hereinbelow.

EXAMPLE 3

Oligomerization of Propylene-Palladium Catalyst Complex

252 Mgs of palladium bis(pentafluorophenylthiolate) and 5.83 gr of chloro benzene are reacted with 520 mgs of 25 wt. % diethyl aluminum chloride in toluene under propylene pressure as in Example 2. 9.22 Gr of products were obtained from the reaction whose distribution is shown in Table 1 hereinbelow.

EXAMPLE 4

Oligomerization of Propylene

22 Mgs of potassium t-butoxide were slurried together with 40 mgs of pentafluorothiophenol in 5.5 grams of chlorobenzene. 62 Mgs of nickel 2-ethylhexanoate trifluoroacetate were added after several minutes. After further stirring, 312 mgs of 25 wt. % ethyl aluminum chloride in toluene are added and the red solution is sealed into a bomb along with 5 grams of propylene. The reaction is continued at 75° C. for 4 hours, then analyzed by gas chromatography. 1.9 Grams of oligomers were obtained whose distribution is shown in Table 1.

EXAMPLE 5

Comparison Oligomerization of Propylene

62 Mgs of nickel 2-ethylhexanoate trifluoroacetate (referred to in U.S. Pat. No. 4,366,087 as nickel 2-ethyl hexanoate trifluoroacetate) in 2 grams of heptane were reacted with 180 mgs of diethyl aluminum chloride under propylene pressure as in Example 2 at 42° C. for 2 hours. 140 Grams of products were obtained whose distribution is shown in Table 1. Only a minor fraction of each oligomer is linear olefins.

The products obtained in Examples 2-5 were analyzed for olefin distribution and linearity (straight chain olefins).

The olefin distribution and percent linearity of each olefin fractin of the products of Examples 2-5 are sum- As can be seen from the above Table, Examples 2-4 using the present invention afforded oligomer products having a high degree of linearity, whereas Example 5 using the same nickel salt catalyst complex, but lacking the fluoroorganic thiolate complexing agent, produced a product having poor linearity and also having a substantially different olefin distribution.

EXAMPLE 6

Oligomerization of Hexene

31 Mg of nickel 2-ethylhexanoate trifluoroacetate were dissolved in 4 grams of n-hexenes and 36 mg of diethyl aluminum chloride were added to this solution. The reaction was stirred at 65° C. for 5 hours. An aliquot was removed for g.c. analysis. This indicated that 0.23 gr of hexene had been converted to oligomers with 97% selectivity to dodecenes. Hydrogenation of these olefins indicates that the dodecenes consist of 79% mono- and unbranched structures, and 21% doubly branched dodecenes.

EXAMPLE 7

Oligomerization of Hexene

46 Mg of nickel bis(pentafluorophenylthiolate) were added to 4 gr of n-hexenes and 36 mgs of diethyl aluminum chloride. The reaction and analysis were run identically to Example 6. 0.7 Gr of hexenes had been converted to oligomers consisting of 94% dodecenes. Hydrogenation of these olefins indicates that the dodecenes consist entirely of mono- and unbranched structures.

Obviously, many modifications and variations of the invention described hereinabove and below can be made without departing from the essence and scope thereof.

What is claimed is:

1. A catalyst composition comprising (1) a transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoroorganic thiol or sulfide does not contain any other ligating group or atom in a ligating position which will displace fluoro as a ligand, and (2) an organometallic-reducing agent selected from the group of borohydride and organoaluminum halides and alkoxides having the formula R* AlX$_n$ wherein R* is alkyl, aryl or arylalkyl; X is fluoride, chloride, bromide, iodide or alkoxide and m is 1 or 2 and n is 3—m.

2. The catalyst composition of claim 1 wherein said fluoro-organic thiol or sulfide is selected from the group having the formula $R_1SR$ wherein $R_1$ is fluoroalkyl having 1 to 18 fluoro atoms and 1 to 8 carbon atoms; fluoroaryl having 6 to 10 carbon atoms and 1 to 6 fluoro atoms; fluoroalkenyl having 2 to 8 carbon atoms and 1 to 16 fluoro atoms; fluoroalkanoyl having 2 to 8 carbon atoms and 1 to 15 fluoro atoms, fluoroalkanoylalkylene having 1 to 17 fluoro atoms and having 2 to 8 carbon atoms in the alkanoyl moiety and 1 to 6 carbon atoms in the alkylene moiety or fluorobenzoyl having 1 to 5 fluoro atoms or a substituted group selected from the fluorosubstituted groups set forth above with respect to $R_1$, further substituted with 1 to 6 substituents independently selected from the group of lower alkyl, lower haloalkyl having 1 to 4 halo substituents, halo, lower haloalkenyl having 1 to 4 halo substituents, or lower alkoxy; and R is hydrogen, $C_1$–$C_8$ alkyl; $C_2$–$C_8$ alkenyl, aryl having 6 to 10 carbon atoms or arylalkyl, having 6 to 10 carbon atoms in aryl moiety and 1 to 4 carbon atoms in the alkyl moiety; alkanoyl having 2 to 8 carbon atoms; alkanoylalkylene having 2 to 8 carbon atoms in the alkanoyl moiety and 1 to 4 carbon atoms in the alkylene moiety; or a substituted group selected from the same groups as set forth hereinabove with respect to R substituted with from 1 to 6 substituents indipendently selected from the group of lower alkyl, lower haloalkyl having 1 to 4 halo substituents, halo, lower haloalkenyl having 1 to 4 halo substituents or lower alkoxy.

3. The catalyst composition of claim 1 wherein said fluoro-organic thiol or sulfide is selected from the group of pentafluorophenylthiol; (lower alkyl)thio-pentafluorobenzene; trifluorothioacetic-S-acid, and ortho-fluoro benzene thiol.

4. The catalyst composition of claim 1 wherein said reducing agent is selected from the group of borohydride and compounds having the formula $R'_m AlX'_n$ wherein $R'$ is lower alkyl having 1 to 6 carbon atoms, phenyl or benzyl; $X'$ is chloro or bromo, m is 1 or 2 and n is 3−m.

5. The catalyst composition of claim 1 wherein said transition metal complex is nickel complexed with a ligand of pentafluorophenylthiol; (loweralkyl)thio-pentafluorobenzyl; or trifluorothioacetic-S-acid.

6. The catalyst composition of claim 1 wherein said reducing agent is selected from the group of borohydride, diethylaluminum ethoxide; and ethylaluminum sesquichloride.

7. The catalyst composition of claim 1 wherein said transition metal complex is a nickel complex.

8. The catalyst composition of claim 1 wherein said transition metal complex is a palladium complex.

9. The catalyst composition of claim 1 wherein said fluoro-organic thiol or sulfide is selected from the group of pentafluorophenylthiol; methyl pentafluorophenyl mercaptan; and ortho-fluorobenzenethiol.

10. The catalyst composition of claim 9 wherein said reducing agent is selected from the group of borohydride, diethylaluminum ethoxide; and ethylaluminum sesquichloride.

* * * * *

UNITED STATES PATENT AND TRADEMARK OFFICE
CERTIFICATE OF CORRECTION

PATENT NO. : 4,757,042
DATED : July 12, 1988
INVENTOR(S) : Richard S. Threlkel

It is certified that error appears in the above-identified patent and that said Letters Patent are hereby corrected as shown below:

Claim 1, Col. 8, line 64, "$R*AlX_n$" should read --$R*_m AlX_n$--

Claim 2, Col. 9, line 24, "indipendently" should read --independently--

Signed and Sealed this

Twenty-fourth Day of January, 1989

Attest:

DONALD J. QUIGG

Attesting Officer      Commissioner of Patents and Trademarks